United States Patent
Zambrano Burgl et al.

(10) Patent No.: US 9,222,076 B2
(45) Date of Patent: Dec. 29, 2015

(54) PROCESS FOR THE PRODUCTION OF PATCHES OR DERSSINGS OF AUTOLOGOUS SKIN THROUGH CULTIVATION OF AUTOLOGOUS KERATINOCYTES AND FIBROBLASTS WITH AUTOLOGOUS SERUM FOR THE GENERATION OF SKIN

(75) Inventors: Juan Carlos Zambrano Burgl, Bogota (CO); Jennifer Cristina Gaona Silva, Bogota (CO)

(73) Assignee: RODRIGO FOCION SOTO PAREJA (CO)

( * ) Notice: Subject to any disclaimer, the term of this patent is extended or adjusted under 35 U.S.C. 154(b) by 2 days.

(21) Appl. No.: 13/699,203

(22) PCT Filed: May 21, 2010

(86) PCT No.: PCT/IB2010/001215
§ 371 (c)(1),
(2), (4) Date: Mar. 28, 2013

(87) PCT Pub. No.: WO2011/144956
PCT Pub. Date: Nov. 24, 2011

(65) Prior Publication Data
US 2013/0195958 A1     Aug. 1, 2013

(51) Int. Cl.
*A61L 15/00*   (2006.01)
*C12N 5/00*    (2006.01)
*C12N 5/071*   (2010.01)

(52) U.S. Cl.
CPC ............ *C12N 5/0698* (2013.01); *C12N 5/0629* (2013.01); *C12N 2502/1323* (2013.01); *C12N 2533/54* (2013.01)

(58) Field of Classification Search
None
See application file for complete search history.

(56) References Cited

FOREIGN PATENT DOCUMENTS

| AU | WO91/16010 | * 10/1991 | ............. A61F 2/10 |
|---|---|---|---|
| WO | 0105942 A2 | 1/2001 | |

OTHER PUBLICATIONS

Concha M et al. "Autologous Dermo-Epidermal Equivalent Production For Treating Big Burns And Keloid Scars" Cuad. Cir. 2002, vol. 16, pp. 41-47.
D. Wisser et al. "Skin Replacement With A Collagen Based Dermal Substitute, Autologous Keratinocytes And Fibroblasts In Burn Trauma" Burns 29 (2003) 375-380.
G. Hinterhuber, et al "Organotypic Keratinocyte Coculture Using Normal Human Serum: An Immunomorphological Study At Light And Electron Microscopic Levels"; Experimental Dermatology 2002: 11: 413-420.
H. P. Ehrlich, Ph.D., "Understanding Experimental Biology Of Skin Equivalent: From Laboratory To Clinical Use In Patients With Burns And Chronic Wounds" The American Journal of Surgery, 187 (Suppl to May 2004) 29S-33S.
International Search Report ; International Application No. PCT/IB2010/001215; International Filing Date: May 21, 2010; 3 pages.
J. F. Hansbrough, Md et al. "Burn Wound Closure With Cultured Autologous Keratinocytes And Fibroblasts Attached To A Collagen-Glycosaminoglycan Substrate" JAMA, Oct. 20, 1989; vol. 262, No. 15; 2125-2130Downloaded: www.jama.com on Sep. 1, 2010.
J. Normand, et al., "A Method For The Isolation And Serial Propagation Of Keratinocytes, Endothelial Cells, And Fibroblasts From A Single Punch Biopsy Of Human Skin" In Vitro Cell. Dev. Biol-Animal 31:447-455, Jun. 1995.
M. Balasubramani et al., "Skin Substitutes: A Review", Burns 27 (2001) 534-544.
S. Negri et al., "Human Plasma As A Dermal Scaffold For The Generation Of A Completely Autologous Bioengineered Skin", Journal of Clinical Rehabilitative Tissue Engineering Research; Nov. 19, 2009 vol. 13, No. 47; 9211-9216.
Written Opinion; International Application No. PCT/IB2010/001215; International Filing Date: May 21, 2010; 13 pages.

* cited by examiner

*Primary Examiner* — Karen Cochrane Carlson
*Assistant Examiner* — Natalie Moss
(74) *Attorney, Agent, or Firm* — Cantor Colburn LLP

(57) ABSTRACT

The process in general is based on taking a sample of skin and a sample of blood from the patient and based on these two elements skin is cultured, being placed on a collagen patch to produce a dressing which is subsequently placed on the patient requiring same.

13 Claims, 7 Drawing Sheets

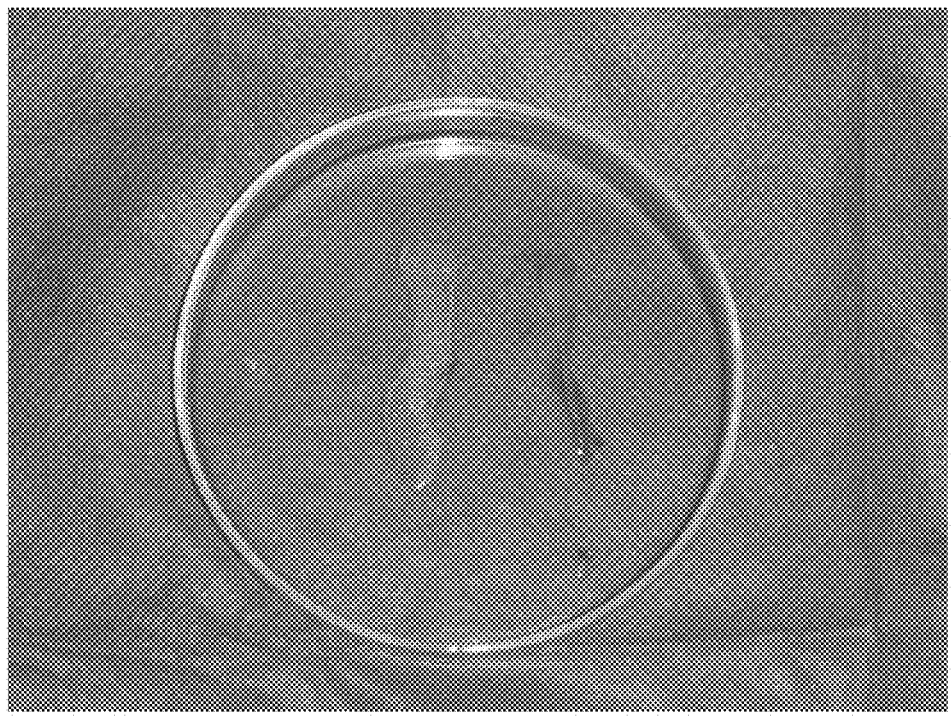
Fig. 1 Skin separation after digestion.
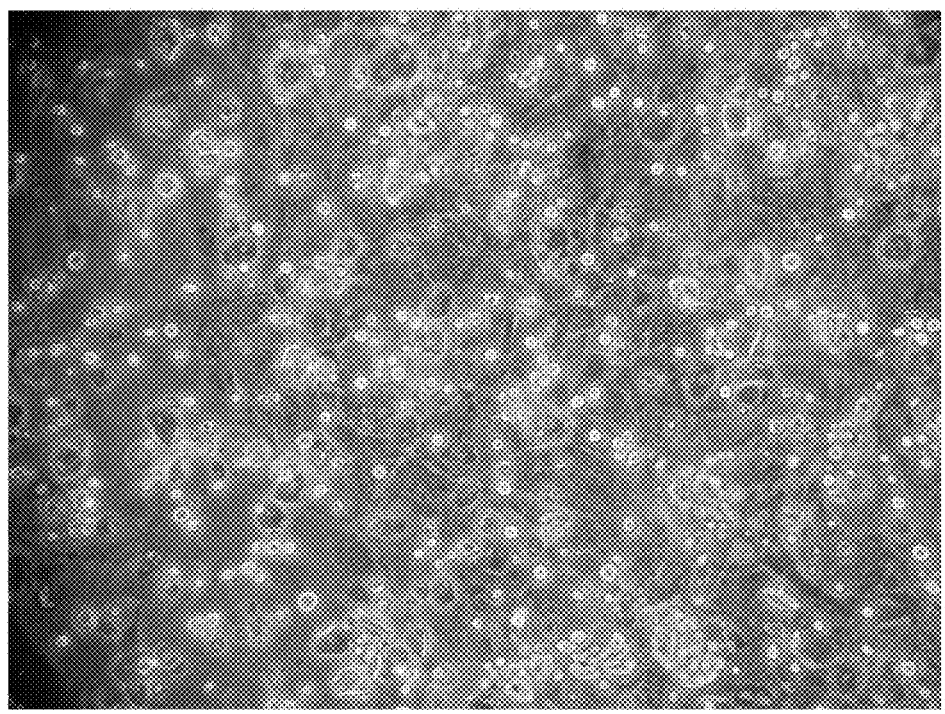
Fig. 2 Keratinocytes mono-layer after 96 hours growth

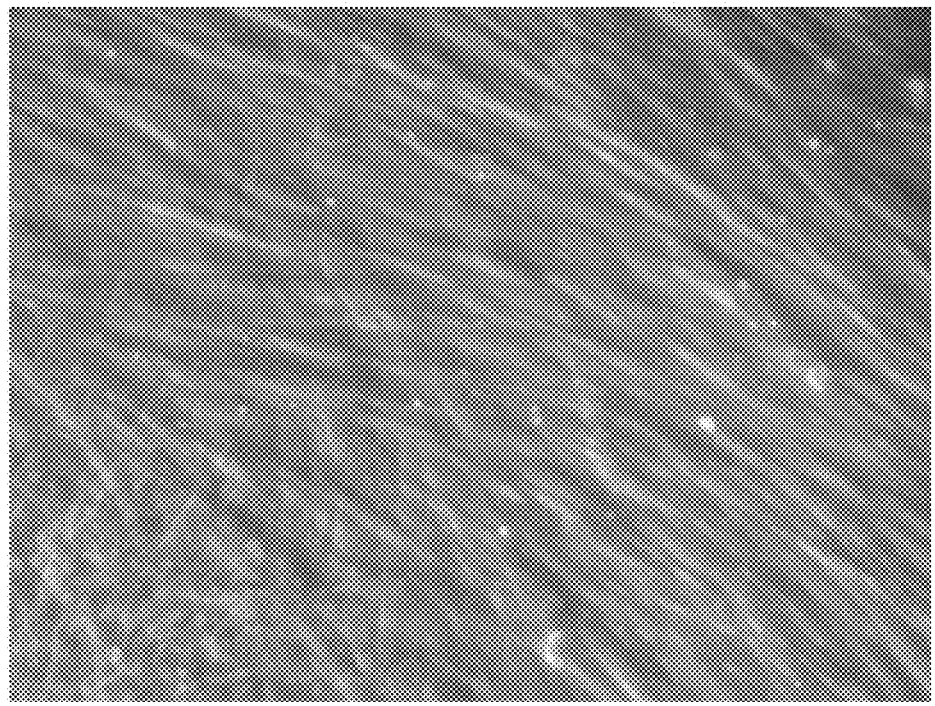
Fig. 3 Keratinocytes over fibroblasts
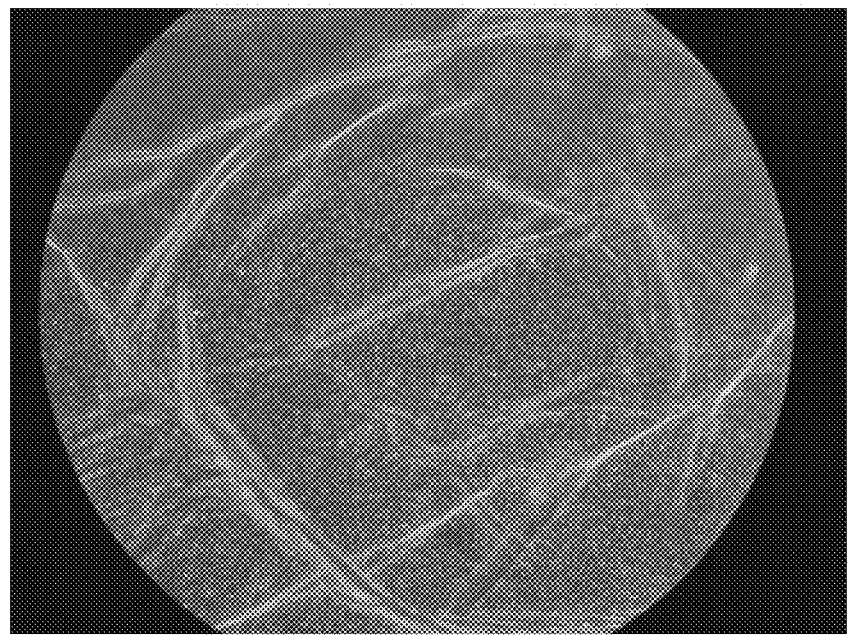
Fig. 4. Collagen dressings with fibroblasts and Keratinocytes

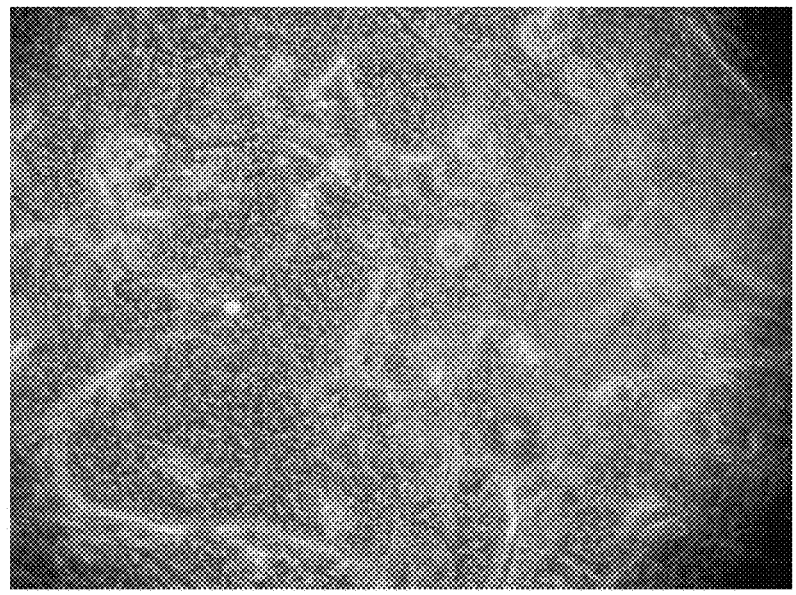
Fig. 5 Keratinocytes and fibroblasts culture status with patient's autologous serum over the collagen mesh. See the adequate cellular confluence and adhesión.

Fig. 6  56 years old patient with a second degree burn in his stomach handled with autologous Keratinocytes culture, showing a complete epitheliazation on the fifth day.

Fig. 7 Patient with a burn in his forearm handled with autologous Keratinocytes culture. Notice (C) the dressing aspect on the third day, adhered and how the same is removed by itself as epitheliazation increases until completely loose with the result of complete wound closure (D).

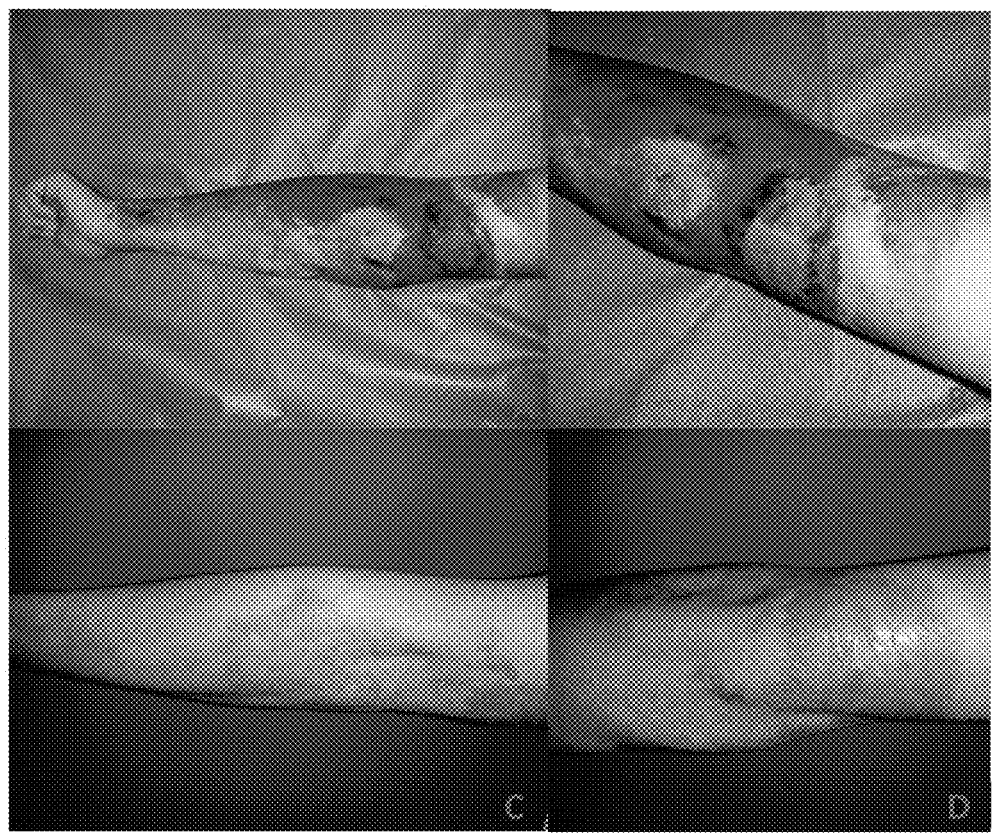

Fig. 8 (A) patient with a second degree deep superficial and deep burn in his upper member with a residual bloody area in the arm (B) residual bloody area covered with dressings (C) Complete epitheliazation on the fifth day. Notice that the cicatrized zone in the second intent shows an hypertrophic scar (D) Area handled with the dressings, which shows a non-indurated planar scar after 7 months of being treated.

Fig 9. 10 years old patient with a burn in the dorsum of the foot whom was treated with the product obtained through the process of the present invention. 6 month follow up process show a planar and slightly pigmented scar but without showing induration.

PROCESS FOR THE PRODUCTION OF PATCHES OR DERSSINGS OF AUTOLOGOUS SKIN THROUGH CULTIVATION OF AUTOLOGOUS KERATINOCYTES AND FIBROBLASTS WITH AUTOLOGOUS SERUM FOR THE GENERATION OF SKIN

TECHNICAL FIELD

The present invention relates to a process for forming skin dressings or patches for coating, healing, cicatrizing, lessen cutaneous loss in patients. In particular, the present invention relates to a process for producing skin carried out in a laboratory.

BACKGROUND

Currently deep burns, as well as other cutaneous tissue losses due to different traumas or diseases, cause skin injuries which require care coating these areas. Such coating has been carried out with skin grafts directly obtained from the patient's own skin. The process, although effective, generates an important scar in the area where the graft is obtained (thighs, back, buttocks) (photo 1). Furthermore, this process must be carried out under surgery with general or partial anesthesia which generates inherent complications to any surgery procedure such as: severe pain, infection, and bleeding, new surgeries and, although in a very low percentage, death. In addition, it also implies high additional economic expenses such as hospitalization, consultations for healing, treatments of the scars of the donor area, special materials for surgery and transportation of the patient to more complex hospitals, among others.

Skin avulsions cause injuries to cutaneous epithelial tissue causing cell losses, which are replaced with a fibrous matrix produced with fibroblasts which act as feeding layer on in vivo conditions. There are several reports related to keratinocytes culture for constructing skin regenerative patches, all such reports talk about cells provided by donors or from dead bodies (heterologous), which implies carrying out multiple studies both to donors and receptors, cultured in bovine fetal serum, which makes this product costly and unviable in developing countries, thus keratinocytes culture was developed in the own patient serum (autologous), on fibroblasts of the same patient (autologous) as the feeding layer, and using keratinocytes of the same patient (autologous), thus avoiding immunologic and rejection reactions when coating the bloody areas thus improving cutaneous viability in invasive processes and obtaining through this means a complete epithelialization (skin growth) in a very short time, with excellent results and very low costs.

Accordingly, alternative mechanisms for coating affected areas have been object of search worldwide. Within same, the process for creating skin is highlighted, allowing replacement of lost skin, and avoiding the entire previously mentioned trauma. Up to the moment, such process was developed using cell from dead bodies, but the process had some drawbacks because using cell from dead bodies created in many cases an immunologic reaction which could generate tissue rejection and low satisfactory results. Additionally, the cost of these processes are very high because using skin from a dead body implies the performance of multiple immunologic compatibility examinations and others carried out for eliminating the possibility of contagious diseases such as HIV and Hepatitis.

SUMMARY OF THE INVENTION

Since 2008, a group of surgeons and plastic surgeons started the task of searching a way for creating skin avoiding the previously mentioned complications. Thus they decided to investigate a way for creating skin from a very small portion (3 mm) of the skin of the affected person, thus guaranteeing the benefits of using cultured tissue and avoiding the disadvantages of incompatibility risks, high costs and additional scars.

The advantages of our process for creating skin from cells taken from the patient have very important implications for science and the future of plastic surgery and medicine worldwide. Among these, it is important to highlight:

1. The process does not create additional scars than the cutaneous injury as the skin taken from the patient in minimum and from invisible locations.
2. Does not cause trauma to patients thus no pain is generated.
3. Does not have the immunologic rejection problems as the used tissues are taken from the same patient.
4. It is not a requirement to carry out the process as a surgery.
5. The process can be handled by nurses and physicians of any specialty.
6. It is not necessary that the hospital wherein the patient is being treated, acquires special material for taking skin (called Dermatome), and the cutting instrument thereof, which are costly as they can only be used once. These products are not necessary on the skin culture process of the present invention.
7. The production cost is around 80% cheaper than that of skin from a dead body and esthetic results are much better.
8. The production and distribution cost is 50% lower than the cost of a chirurgic procedure on a 20×20 cm area.

This is a process which, with a basic training, is replicable in any place of the world, included developing countries, because all used materials are those of common and basic use in any laboratory.

A brief comparative analysis, given below, will show the state of the art in various embodiments in view of the present invention. The goal of said analysis is to highlight the advantages of the present invention which grant the necessary characteristics for obtaining the claimed patent title.

There is an ample documentation showing the state of the art wherein the used processes are well detailed and based in those cited documents, a detailed comparison can be carried out with the present invention arriving to the above exposed conclusions. Said references will be given below, and can be consulted.

Since long ago different method for cell culture for use as coatings of bloody skin areas and/or cutaneous substitutes are being developed. The novelty in the product of the present invention is that is produced from autologous cells using the same patient's serum (autologous), obtaining skin layers in just three days. Among the other method we find:

1. Human Skin Equivalent

A. Donor or Dead Body Cell Culture

This method differs from that developed in the present invention in that samples are provided from skin portions of dead bodies or donors and through a cryogenics and preservation process requiring multiple chemicals and compounds, which freezed skin portions are stored for a later application in patients requiring same. This needs immunologic studies both of donors and patients in order to reduce the rejection risk. The main differences are:

| THE PRESENT INVENTION PRODUCT | DONOR OR DEAD BODY CULTURE |
|---|---|
| Patient's own cells | Skin from donor or dead body |
| Autologous serum | Bovine fetal serum and glycerol and dimethyl sulfoxide |
| Autologous serum | Growth factors, insulin, interleukins, thrombin |
| Permanent coating | Temporal dressing |
| No further processes required | Requires additional skin grafts |
| Obtained in three days | Is stored and ready for use |
| Does not require additional laboratory tests | Requires immunologic, CMV and anti-HTLV1, Hepatitis B, HIV, serology, kidney hepatic tests, and bacteriologic skin cultures. |
| No disease transmission | May transmit diseases |
| No donors needed | Donors needed |
| No donors needed | Donors having less than 75 years old and death time less than 6 hours |
| Skin extraction is carried out in any room | Skin extraction is carried out in sterile environment |
| Requires storage at –4° C. in any conventional refrigerator | Storage must be carried out in a freezer at –80° C. Requires Cryopreservation |
| Does not require any special process when applying it | Must be unfreezed and washed in serum prior to application |
| Low cost | High cost |
| No rejection problem | There is always a rejection problem |

B. Compounds Based in Synthetic Collagen and Synthetic Dermal Analogous

This is a completely different process from ours as these are temporal dressings (no permanent) produced from synthetic or animal compounds. Do not take cells from either serum or human beings. The products are stored and immediately available at different costs and trade names in the market. Among these we find Biobrane, Transyte, Integra, Alloderm, Allograf, Apligraf and Demalogen.

2. Keratinocytes Cell Culture

Cell cultures have been developed since around three decades and now it is even possible to cultivate dermic cells from mother cells, thus dermic cells can be easily produced. The most marked differences with the other cell culture methods is that the present invention obtains a dressing having the required size in only three days with enough keratinocytes confluence for coating bloody areas while the other method take at least 3 weeks in the case of autologous keratinocytes culture.

In addition, our method does not require donor nor additional studies because we use both cells and serum from the same patient, a thing that nobody does.

| THE PRESENT INVENTION PRODUCT | HETEROLOGOUS KERATINOCYTES | AUTOLOGOUS KERATINOCYTES |
|---|---|---|
| Patient's own cells | Donor cells | Patient's own cells |
| Autologous serum | Bovine fetal serum | Bovine fetal serum |
| Autologous serum | Growth factors, insulin, interleukins, thrombin | Growth factors, insulin, interleukins, thrombin |
| Permanent coating | Occasionally may need skin graft | Occasionally may need skin graft |
| No further processes required | Occasionally may need skin graft | Occasionally may need skin graft |
| Obtained in three days | Obtained between 3 to 4 weeks | Obtained between 3 to 4 weeks |
| Does not require additional laboratory tests | Requires immunologic, CMV and anti-HTLV1, Hepatitis B, HIV, serology, kidney hepatic tests, and bacteriologic skin cultures. | Requires bacteriologic cultures |
| No disease transmission | May transmit diseases | No disease transmission |
| No donors needed | Donors needed | |
| No donors needed | Donors are needed | No donors needed |
| No rejection problem | There may be a rejection problem | No rejection problem |

BIBLIOGRAPHIC REFERENCES

1. Kultivierte keratinozyten: gestern-heute. Bettina bierbocks, k. Pickl-herk, r. Soller, g s bayer, g. Meissl, m frey.
2. Estandarizacion de un metodo de cultivo de queratinocitos primarios y su co cultivo con fibroblastos en mallas de colageno i. Posada maria mercedes, fontanilla marta raquel.
3. Kolf, c. m.; cho, e.; tuan, r. s. 2007. Biology of adult mesenchymal stem cells: regulation of niche, self-renewal and differentiation. In: http://arthritis-research.com/content/9/1/204. Consulted: Oct. 29, 2007
4. Myers, s. r.; leigh, i. m.; naysaria, h. 2007. Epidermal repair results from activation of follicular and epidermal progenitor keratinocytes mediated by a growth factor cascade. Wound rep. Reg. 15, 693-701.
5. Staiano-coico, l; higgins, p. j.; darzynkiewicz, z.; kimmel, m.; gottlieb, a. b.; pagan-charry, i.; madden, m. r.; finkeistein, hefton, j. m. 1986. Human keratinocyte culture: identification and staging of epidermal cell subpopulations. J. Clin. Invest. 77, February, 396-404.
6. Jiao, xiang-yang m. d.; tanczos, eszter m. d.; dodic, tom; voigt, mathias m. d.; haberstroh, joerg vet. M. d.; stark, g. Bjorn m. d. prefabrication of bilaminar-epithelialized composite flap with tissue expander and cultured keratinocytes. Plastic & reconstructive surgery. 103(1):138-144, January 1999.
7. Kangesu, thirloshan m. s., f. r. c. s. (plast.); manek, sanjiv m. r. c. path.; terenghi, giorgio ph. d.; gu, xu-hong b. sc.; naysaria, harshad a. M. sc. Nerve and blood vessel growth in response to grafted dermis and cultured keratinocytes. Plastic & reconstructive surgery. 101(4):1029-1038, April 1998.
8. Pandya, a. N. M. s., m. ch. (plast.), dip. nat. board (gen.) (plast.), f. r. c. s.(edin.), f. r. c. s. (glas.); woodward, b. Ph. d.; parkhouse, n. D. m. the use of cultured autologous keratinocytes with integra in the resurfacing of acute burns. Plastic & reconstructive surgery. 102(3):825-828, September 1998.
9. Magnusson, mark f. r. a. c. s. (plast.); papini, remo p. F. r. c. s. (plast.); rea, suzzane m. F. r. c. s. i. (plast.); reed, chris c. B. sc. (eng.); wood, fiona m. Cultured autologous keratinocytes in suspension accelerate epithelial maturation in an in vivo wound model as measured by surface electrical capacitance. Plastic & reconstructive surgery. 119(2):495-499, February 2007.
10. Simman, richard m. d.; talisman, ran m. d.; soroff, harry s. M. d.; hatch, gabriele a. b.; simon, marcia ph. d. cultured palmar keratinocytes after auto-engraftment to plantar surface maintain site and function specificity. Plastic & reconstructive surgery. 104(1):175-179, July 1999.
11. Butler, charles e. M. d.; orgill, dennis p. M. d., ph. d.; yannas, ioannis v. Ph. d.; compton, carolyn c. M. d., ph. d. effect of keratinocyte seeding of collagen-glycosaminoglycan membranes on the regeneration of skin in a porcine model. Plastic & reconstructive surgery. 101(6):1572-1579, May 1998.
12. imaizumi t, asahina i, moriyama t, ishii m, omura k. Cultured mucosal cell sheet with a double layer of keratinocytes and fibroblasts on a collagen membrane. Tissue eng. 2004 May-June; 10(5-6):657-64.
13. Smirnov s v, Kiselev i v. Rogovaya o s, Vasil'ev a v, Ierskikh v v, Skin repair by transplantation of cultured keratinocytes. Bull exp biol med. 2003 June; 135(6):608-9.
14. Voigl m, Schauer m, Schaefer d j, andree c, horch r, stark g b, Cultured epidermal keratinocytes on a microspherical transport system are feasible to reconstitute the epidermis in full-thickness wounds. Tissue eng. 1999 December; 5(6):563-72.
15. Beli e, Sher s, Hull b, Merrill c, Rosen s, Chamson a, asselineau d, dubertret l, coulomb b, lapiere c, nusgens b, neveux y. The reconstitution of living skin. J invest dermatol. 1983 July; 81(1 suppl):2s-10s
16. A. w. c. chua, d. r. ma, i. c. song, t. t. phan, s. t. lee and c. Song in vitro evaluation of fibrin mat and Tegaderm™ wound dressing for the delivery of keratinocytes—implications of their use to treat burns *burns, in press, corrected proof*, available online 29 Oct. 2007
17. Bishara s. Atiyeh and michel costagliola cultured epithelial autograft (cea) in burn treatment: three decades later *burns, volume* 33, *issue* 4, June 2007, pages 405-413
18. D. d. lozano the effect of a fibroblast derived skin substitute on keratinocyte proliferation *burns, volume* 33, *issue* 1, *supplement* 1, February 2007, pages s62-s63
19. Matthias rab, rupert koller, margot ruzicka, gudrun burda, lars peter kamolz, bettina bierochs, guenther meissl and manfred frey. Should dermal scald burns in children be covered with autologous skin grafts or with allogeneic cultivated keratinocytes?—"the viennese concept" *burns, volume* 31, *issue* 5, August 2005, pages 578-586
20. L. p. kamolz, m. Luegmair, n. Wick, b. Eisenbock, s. Burjak, r. Koller, g. Meissl and m. Frey. the viennese culture method: cultured human epithelium obtained on a dermal matrix based on fibroblast containing fibrin glue gels *burns, volume* 31, *issue* 1, February 2005, pages 25-29
21. C.-j. Gustafson and g. Kratz. Cultured autologous keratinocytes on a cell-free dermis in the treatment of full-thickness wounds. *Burns, volume* 25, *issue* 4, June 1999, pages 331-335
22. J. E. Paddle-Iedinek, d. G. Cruickshank and j. P. Masterton. Skin replacement by cultured keratinocyte grafts: an australian experience *burns, volume* 23, *issue* 3, May 1997, pages 204-211

BRIEF DESCRIPTION OF THE DRAWINGS

FIG. 1 shows a photograph of the skin separation after digestion.
FIG. 2 is a view of the keratinocytes mono-layer after 96 hours growth.
FIG. 3 shows the keratinocytes over fibroblasts.
FIG. 4 shows a view of how the collagen dressings with fibroblasts and keratinocytes.
FIG. 5 shows the keratinocytes and fibroblasts culture in patient's autologous serum placed on a collagen mesh.
FIG. 6 show a 56 years old patient with a second degree burn in his stomach whom was treated with a product of the present invention, showing complete epithelialization on the fifth day.
FIGS. 7 A-D show a patient with a burn in his forearm whom was treated with the product obtained through the process of the present invention. FIG. 7C shows the aspect of the dressing adhered on the third day and how the same is removed by itself as epithelialization increases until completely loose with the result of a complete wound closure as shown in FIG. 7D.
FIGS. 8 A-D show the evolution of a patient with a second degree deep superficial and deep burn in his upper member with a residual bloody area in the arm whom was treated with the product obtained through the process of the present invention.
FIGS. 9 A-D show the evolution of a 10 years old patient with a burn in the dorsum of the foot whom was treated with the product obtained through the process of the present invention. 6 month follow up process show a planar and slightly pigmented scar but without showing induration.

DETAILED DESCRIPTION IF THE INVENTION

The present invention relates to a process for forming skin dressings or patches for coating, healing, cicatrizing, lessen cutaneous loss in patients. Said process is described below based on an exemplary embodiment provided to explain the invention as to understand the same in all its scope and spirit. It must be understood that numerous variations can be obtained by those skilled in the art which fall within the scope and spirit of the present invention. Said scope is only determined by the annexed claims.

The process, in general, is based in obtaining a skin sample and a blood sample of the patient and with these two elements the skin is cultured, which is placed on a collagen patch thus producing a dressing which further on will be used on a patient when required. Said process comprises two sub-processes which can be carried out simultaneously or sequentially, although the simultaneous way is preferred to perform the sub-processes. One sub-process starts in step 10 for treating the superficial skin and the other sub-process starts simultaneously or following in step 10'. Thus, the process of the invention will be describe with the following steps:

I—*Day 0:
  A—Obtaining a autologous skin and blood samples.
    1—Obtaining from the patient a skin sample, having an area between 2 mm² and 4 mm², preferably 3 mm² and a thickness between 0.30 mm to 0.65 mm,
    2—Obtaining a blood sample in an amount of around 20-50 cm³ from the individual requiring the skin (autologous).
  B—Digestion of the skin (18 hours)
    3—Washing the obtained skin sample with around 2 cm³ and 10 cm³ of a phosphate buffer solution (PBS).
    4—Placing the autologous skin sample into a 0.25% tripsine solution during 18 hours at 4° C.
  C—Obtaining autologous serum from the patient's blood
    5—Centrifuging the autologous blood sample during 10 minutes at 1200 rpm obtaining between 10 cm³ to 25 cm³ of plasma.
    6—Storing said plasma at 4° C.
    7—Inactivate the applied Tripsine through adding 2 cm³ to 5 cm³ of DMEM-HG (Dulbecco modified Eagle Medium—High Glucose), 2 cm³ to 5 cm³ of a phosphate Buffer solution (PBS) and 0.5 cm³ to 2 cm³ of 10,000 I.U. penicillin, 10 mg of streptomycin Sulfate and 25/−1 g of Amphotericin B.
II—*Day 1:
  D—Separating the two layer of autologous skin. (See FIG. 1)
    8—Then separating the autologous skin in two layers (explants) through the help of tweezers: a superficial epidermis and a deep layer of dermis containing collagen fibers.
    9—Separately washing the explants (the two skin layers) several times (between 3 and 10 times) with phosphate Buffer solution (PBS). ***;

E—Culture and replication of keratinocytes in autologous serum (72 h) obtained from the superficial layer of autologous skin obtained after digestion.
10—Collecting the superficial portion of the skin in a sterile tube;
11—Centrifuging said tube for 10 minutes at 1200 rpm.
12—Discarding the supernatant;
13—Re-suspend the resulting cell button in 5 cm$^3$ to 10 cm$^3$ of DMEM-HG medium (Dulbecco modified Eagle Medium—High Glucose).
14—Seed the cells contained in this liquid at a density of 75,000 to 90,000 cells/cm$^2$ in sterile boxes;
15—Verifying cellular density through cellular counting in a Neubawer chamber;
16—Storing the seeded cells (keratinocytes) at 37° C. during 24 hours.
F—Culture and replication of autologous fibroblasts obtained from the deep layer resulting after digestion.
10'—Following step 9, seeding the deep portion of the autologous skin obtained after digestion in an sterile box;
11'—adding from 2 cm$^3$ to 5 cm$^3$ of DMEM-HG (Dulbecco modified Eagle Medium—High Glucose) and 2 cm$^3$ to 5 cm$^3$ of plasma obtained from the blood of the individual requiring the skin;
12'—storing the result at 37° C. during 48 hours allowing fibroblasts growth.
13'—extracting and placing in a sterile tube the seeded and stored fibroblasts after 48 hours;
14'—Centrifuging for 10 minutes at 1200 rpm said tube;
15'—Discarding the supernatant;
16'—adding 2 cm$^3$ to 5 cm$^3$ of DMEM-HG (Dulbecco modified Eagle Medium—High Glucose) and 2 cm$^3$ to 5 cm$^3$ of autologous plasma obtained from the blood of the individual requiring the skin, to the cellular button.
III—*Day 2:
G—Changing the culture medium of autologous keratinocytes.
17—Extracting the culture liquid or medium after 24 hours of storage of the keratinocytes culture;
18—Again applying from 2 cm$^3$ to 5 cm$^3$ of DMEM-HG (Dulbecco modified Eagle Medium—High Glucose) plus 1 cm$^3$ to 10 cm$^3$ of autologous plasma (resulting from the patient's blood);
19—Again storing for 24 hours at 37° C. (See FIG. 2)
IV—*Day 3:
H—Seeding the Fibroblasts on a collagen mesh.
20—Seeding the obtained product of step 16' on a collagen mesh of the required size;
21—Checking that the autologous fibroblasts bear a 90% confluence;
22—Placing this mesh on an oscillating table during a minimum of 4 hours;
23—Again storing at 37° C. for minimum 20 hours;
I—Seeding the cultured keratinocytes on the fibroblasts and the collagen mesh (24 h) (See FIG. 3)
24—Separating the keratinocytes, after 24 hours of having replaced the medium and having stored thereof, from the box using 2 cm$^3$ to 10 cm$^3$ of phosphate Buffer solution (PBS);
25—Placing this liquid with the cells in a sterile tube and centrifuging during 10 minutes at 1200 rpm.
26—Discarding the supernatant resulting from centrifuging;
27—Re-suspending the cellular button in 5 cm$^3$ to 10 cm$^3$ of autologous plasma.
28—Seeding the keratinocytes immersed in the plasma on the fibroblasts and the collagen mesh while checking they have a density of 250,000 cells/cm$^2$;
29—Storing the seeded cells at 37° C. during 24 hours;
30—Observing after this time the confluence and cellular adhesion on the collagen dressings thus obtaining an adequate autologous tissue skin layer. (See FIGS. 4 and 5)
V—*Day 4:
J—Handling of the skin dressing for placing same on the individual requiring same.

SUMMARY OR THE PROCESS ACCORDING TO THE INVENTION

I—*Day 0:
A—Obtaining a autologous skin and blood samples.
B—Digestion of the skin (18 hours)
C—Obtaining autologous serum from the patient's blood
II—*Day 1:
D—Separating the two layer of autologous skin
E—Culture and replication of keratinocytes in autologous serum (72 h) obtained from the superficial layer of autologous skin obtained after digestion.
F—Culture and replication of autologous fibroblasts obtained from the deep layer resulting after digestion.
III—*Day 2:
G—Changing the culture medium of autologous keratinocytes.
IV—*Day 3:
H—Seeding the Fibroblasts on a collagen mesh.
I—Seeding the cultured keratinocytes on the fibroblasts and the collagen mesh (24 h)
V—*Day 4:
J—Obtaining the final product such as a skin layer patch or dressing for placing same on the individual requiring thereof.

The result of the application of the described process of the present patent application is a patch or a dressing formed with skin created on a collagen substrate. Said product is directly applied on the cutaneous loss area, which allows the generation of skin on the wound of the patient in a clean and fast manner thus obtaining results such as those described in the following examples and shown in FIGS. 6 to 9.

APPLICATION EXAMPLES AND DEVELOPMENT OF THE INVENTION IN TRUE CASES 10 patients having bloody cutaneous areas were treated in the following manner. First the bloody area was washed and debrided, at that moment a healthy skin sample having 3 mm length was obtained and 20 cm$^3$ of blood was extracted. These materials were sent to the laboratory and the above mentioned process was carried out.

Three days after obtaining the sample, a dressing having fibroblasts and keratinocytes was now available having an adequate cellular density so as to be used (FIG. 5). Another washing step is performed on the bloody area and the dressing is placed covering same with gauze and a transparent dressing. On the fifth day after the explant was placed, the same is removed finding a complete epithelialization in all treated patients (FIGS. 8 and 9).

A photographic follow up of the patients was carried out thus finding that the area treated with autologous keratinocytes showed a better quality scar, with no induration and no retractions, while the areas that healed in a second intention and with healings showed hypertrophy of the scar (FIGS. 6 and 7).

CONCLUSIONS OF THE EXAMPLES AND RESULTS OF THE APPLICATION OF THE INVENTION

Patients having bloody cutaneous areas have been handled through history using different methods and today there are different treatment options from second intention closure to heterologous cell cultures. Heterologous keratinocytes cultures have been developed worldwide and the method for culturing thereof is standardized, but these require immunologic studies when dealing with foreign cells to the host receptor.

In view of such difficulty, we have developed and standardized a method that allows obtaining dressings with keratinocytes and autologous serum out of a very small sample and in three days, obtaining a complete epithelialization on the fifth day, being that scar different to that shown in patient treated with skin grafts or second intention closure in that it does not show contraction or retraction and offers a viable alternative for handling bloody areas with no additional scars on the graft donor areas.

The present invention has been described through an illustrative embodiment of the same. It must be understood that said description must be read as being non-limitative of the invention, as any skilled in the art can introduce changes and modifications which do not fall out of the scope and spirit of the invention, which is only defined by the content of the claims.

The invention claimed is:

1. A process for generating a skin layer patch or a dressing for a patient in need thereof, characterized in that it comprises the steps of:
    obtaining, from a patient requiring a skin layer patch or dressing, an autologous skin sample and a blood sample;
    digestion of the autologous skin sample for 18 hours;
    obtaining autologous serum from the patient's blood sample, separating the digested autologous skin into two layers, a superficial epidermis layer and a deep layer of dermis;
    culturing and replication of keratinocytes in the autologous serum for at least 72 h, wherein the keratinocytes are obtained from the superficial layer of the digested autologous skin;
    culturing and replication of fibroblasts obtained from the deep layer of the digested autologous skin;
    seeding the cultured fibroblasts on a collagen mesh;
    and seeding the cultured keratinocytes on the fibroblast-seeded collagen mesh and then culturing the keratinocyte-seeded collagen mesh for 24 h to obtain the skin layer patch or dressing for the patient.

2. The process according to claim 1, wherein the skin sample obtained from the patient has an area between 2 mm$^2$ to 4 mm$^2$ and a thickness between 0.30 mm and 0.65 mm; and the blood sample obtained from the patient, has a volume of 20 to 50 cm$^3$.

3. The process according to claim 1, characterized in that digestion of the autologous skin sample comprises the steps:
    washing the autologous skin sample with between 2 cm$^3$ and 10 cm$^3$ of a phosphate buffer solution (PBS);
    and placing the washed autologous skin sample into a 0.25% trypsin solution for 18 hours at 4° C.

4. The process according to claim 1, characterized in that obtaining autologous serum from the patient's blood sample comprises the steps:
    centrifuging the autologous blood sample for 10 minutes at 1200 rpm obtaining between 10 cm$^3$ to 25 cm$^3$ of plasma;
    storing said plasma at 4° C.

5. The process according to claim 3, characterized in that separating the digested autologous skin into two layers comprises the steps:
    inactivating the trypsin solution;
    separating the autologous skin into the two layers using tweezers;
    separately washing the two skin layers between 3 and 10 times with phosphate buffer solution (PBS).

6. The process according to claim 1, characterized in that culturing and replication of keratinocytes in the autologous serum comprises the steps:
    collecting the superficial epidermis layer of the skin in a sterile tube;
    centrifuging said tube for 10 minutes at 1200 rpm;
    discarding the supernatant;
    re-suspending the resulting cell pellet comprising keratinocytes in 5 cm$^3$ to 10 cm$^3$ of DMEM-HG medium (Dulbecco modified Eagle Medium—High Glucose);
    seeding the keratinocytes contained in this medium at a density from around 75,000 to 90,000 cells/cm$^2$ in sterile boxes;
    storing the seeded keratinocyte culture at 37° C. for 72 to 120 hours.

7. The process according to claim 1, characterized in that culturing and replication of fibroblasts comprises the steps:
    seeding the deep layer in a sterile box;
    adding from 2 cm$^3$ to 5 cm$^3$ of DMEM-HG (Dulbecco modified Eagle Medium—High Glucose) and from 2 cm$^3$ to 5 cm$^3$ of autologous plasma obtained from the patient's blood sample;
    storing the result at 37° C. for 48 hours to allow fibroblast growth;
    extracting and placing in a sterile tube the seeded and stored fibroblasts after 48 hours;
    centrifuging for 10 minutes at 1200 rpm said tube;
    discarding the supernatant;
    adding 2 cm$^3$ to 5 cm$^3$ of DMEM-HG (Dulbecco modified Eagle Medium—High Glucose) and 2 cm$^3$ to 5 cm$^3$ of autologous plasma obtained from the patient's blood sample, to the resulting cell pellet.

8. The process according to claim 6, further comprising changing the culture medium of the stored keratinocyte culture after 24 hours of storage at 37° C. by:
    extracting the culture medium after 24 hours of storage of the keratinocyte culture;
    applying from 2 cm$^3$ to 5 cm$^3$ of DMEM-HG (Dulbecco modified Eagle Medium—High Glucose) plus 1 cm$^3$ to 10 cm$^3$ of autologous plasma obtained from the patient's blood sample; and
    storing the keratinocyte culture in the newly applied medium for 24 hours at 37° C.

9. The process according to claim 1, characterized in that seeding the cultured fibroblasts on a collagen mesh further comprises the steps:
    seeding the cultured fibroblasts on a collagen mesh of a size required by the patient;
    checking that the seeded fibroblasts reach a 90% confluence;
    placing the fibroblast-seeded collagen mesh on an oscillating table for a minimum of 4 hours;

storing the fibroblast-seeded collagen mesh at 37° C. for a minimum of 20 hours.

10. The process according to claim 1, characterized in that seeding the cultured keratinocytes on the fibroblast-seeded collagen mesh comprises the steps:
    placing the cultured keratinocytes suspended in phosphate buffer solution (PBS) in a sterile tube and centrifuging for 10 minutes at 1200 rpm;
    discarding the supernatant resulting from centrifuging;
    re-suspending the resulting cell pellet in 5 $cm^3$ to 10 $cm^3$ of autologous plasma;
    seeding the re-suspended keratinocytes on the fibroblasts and the collagen mesh;
    culturing the keratinocyte-seeded mesh at 37° C. for at least 24 hours to achieve cellular confluence and adhesion on the mesh to obtain the skin layer patch or dressing for the patient.

11. The process of claim 3, further comprising
    inactivating the trypsin solution by adding 2 $cm^3$ to 5 $cm^3$ of DMEM-HG (Dulbecco modified Eagle Medium—High Glucose), 2 $cm^3$ to 5 $cm^3$ of a phosphate buffer solution (PBS) and 0.5 $cm^3$ to 2 $cm^3$ of 10,000 I.U. penicillin, 10 mg of streptomycin sulfate and 25/−1 g of Amphotericin B.

12. The process of claim 5, wherein inactivating the trypsin solution comprises
    adding 2 $cm^3$ to 5 $cm^3$ of DMEM-HG (Dulbecco modified Eagle Medium—High Glucose), 2 $cm^3$ to 5 $cm^3$ of a phosphate buffer solution (PBS) and 0.5 $cm^3$ to 2 $cm^3$ of 10,000 I.U. penicillin, 10 mg of streptomycin sulfate and 25/−1 g of Amphotericin B.

13. The process of claim 10, wherein the cultured keratinocytes are seeded at a density of 250,000 cells/$cm^2$.

* * * * *